United States Patent [19]
Evans et al.

[11] Patent Number: 5,525,202
[45] Date of Patent: Jun. 11, 1996

[54] ASSEMBLY METHOD OF AND GLASS PLATE CASSETTE FOR ELECTROPHORESIS

[75] Inventors: Robert Evans, Treasure Island; Mark F. Shon, Largo; Virgil Wheeler, Tampa; Nicolas Neckelmann, Largo, all of Fla.

[73] Assignee: E-C Apparatus Corporation, Holbrook, N.Y.

[21] Appl. No.: 309,014

[22] Filed: Sep. 20, 1994

[51] Int. Cl.$^6$ ............................................. G01N 27/26
[52] U.S. Cl. ............................................. 204/606; 204/456
[58] Field of Search ............................. 204/299 R, 182.8

[56] References Cited

U.S. PATENT DOCUMENTS

| | | | |
|---|---|---|---|
| 4,699,680 | 10/1987 | Shiraishi et al. | 156/242 |
| 4,861,411 | 8/1989 | Tezuka | 156/344 |
| 5,149,417 | 9/1992 | Foley et al. | 204/299 R |
| 5,188,790 | 2/1993 | Magnant | 264/219 |
| 5,281,322 | 1/1994 | Antoinette et al. | 204/299 R |
| 5,324,412 | 6/1994 | Kolner | 204/299 R |

*Primary Examiner*—Arun S. Phasge
*Attorney, Agent, or Firm*—Morrison Law Firm

[57] ABSTRACT

A cassette for containing a gel slab used in an electrophoresis separation comprises a pair of spaced glass or like material plates having spacer strips interposed between marginal side edge areas of the plates to define a space for containing a gel slab between the plates. The spacer strips are made of a flexible double rolled smooth finished polymeric, preferably polyvinyl chloride material which when used for such purpose function to interface under pressing pressure imposed thereon to exclude atmospheric air at the interface so that once interfaced with the plates, atmospheric air pressure acting on the plates maintains a pressed sealed interface condition effective to prevent liquid flow from a liquid-containing gel slab composition cast in the cassette sideways through the cassette during gelation of the composition. An assembly tool and method for effecting cassette assembly is provided.

7 Claims, 4 Drawing Sheets

ASSEMBLY METHOD OF AND GLASS PLATE CASSETTE FOR ELECTROPHORESIS

BACKGROUND OF THE INVENTION

The present invention relates to a cassette for holding a gel slab used in an electrophoresis separation and, more particularly, to such a cassette as is more easily and surely assembled than heretofore practiced and to an end that fluid leakage laterally of the cassette from a liquid-containing gel slab composition cast in the cassette is prevented.

Separation of biological components by electrophoresis separation is well known. In such a separation, electric current flow through a gel slab carries, e.g., DNA, RNA or protein molecules from a source at a negative terminal through the slab towards a positive terminal, the passage of these molecules being identifiable, observable and recordable so as to produce data meaningful to the molecular biologist.

Commonly the gel slab is formed or cast from a gellable composition such as an acrylamide in a cassette comprised of two glass plates juxtaposed spaced by spacer strips at the sides of the plates. During casting, the bottom side of the cassette generally is sealed by the a seal element carried on a casting stand. The spacer strips can be elements adhesively secured to facing sides of the two glass plates as disclosed, for example, in U.S. Pat. No. 4,699,680. Other spacers commonly are of rigid plastic such as nylon and these are clamped together intermediate the two plates at side margins thereof with devices such as screws or like components in quest of establishing fluid proof interface between the plates and the spacers.

The degree of seal possible with the foregoing arrangement is problematical and often ineffective to the end of leakage of liquid from the gel composition and outwardly from the cassette sides. Such leakage also creates soil conditions on the cassette which are messy and difficult to clean.

Further, aligning edge surfaces of the glass plates and spacers in proper sandwich configuration is tedious and if not done with precision is futile since composition leakage almost certainly will occur during casting and before the composition has gelled. In some instances, technicians have sought to prevent leakage during casting by taping the side edges of the cassette before introducing the gel slab composition therein.

OBJECTS AND SUMMARY OF THE INVENTION

Accordingly, it is an object of the invention to provide a cassette for containing a gel slab used in an electrophoresis separation which overcomes the drawbacks of the prior art.

It is a further object of the invention to provide a cassette for containing a gel slab used in electrophoresis separation which is easily and surely assembled in manner as allows subsequent gel formation therein without risk that lateral liquid leakage of casting composition from the cassette will occur during casting.

It is a still further object of the invention to provide a method for assembling such a cassette wherein an alignment tool is employed to assure precise edge alignment of the glass plates and spacer strips at the cassette side edges.

Briefly stated, there is provided a cassette for containing a gel slab used in an electrophoresis separation which comprises a pair of spaced glass or like material plates having spacer strips interposed between marginal side edge areas of the plates to define a space for containing a gel slab between the plates. The spacer strips are made of a flexible double rolled smooth finished polymeric, preferably polyvinyl chloride material which when used for such purpose function to interface under pressing pressure imposed thereon to exclude atmospheric air at the interface so that once interfaced with the plates, atmospheric air pressure acting on the plates maintains a pressed sealed interface condition effective to prevent a liquid flow from a liquid-containing gel slab composition cast in the cassette sideways through the cassette during gelation of the composition. An assembly tool and method for effecting cassette assembly is provided.

In accordance with these and other objects of the invention, there is provided a cassette for containing a gel slab used in an electrophoresis separation, said cassette comprising a pair of hard surfaced plates. The plates each have opposite broad planar faces, a bottom edge and opposite side edges disposed orthogonal to the bottom edge. Spacer means are interposed between the plates for holding said plates juxtaposed with a face of one plate spaced from a face of the other plate so as to define a cassette space into which a liquid-containing gellable composition can be introduced and allowed to gelate to form a gel slab. The plates having identical edge envelopes so that when juxtaposed, the bottom and respective side edges of one plate are in alignment with the bottom and respective side edges of the other plate. The spacer means comprise a pair of relatively thin widened strips of substantially uniformly thick flexible polymeric material presenting opposite flat faces and arranged with one strip extending at least coextensively with one aligned pair of plate side edges and the other strip extending at least coextensively with the other aligned pair of plate side edges. Each strip has a longitudinal side edge aligned with corresponding plate side edges, the polymeric strip material being further characterized by being a smooth polish finished faced component so that when a squeeze together force is imposed on side edge marginal portions of the juxtaposed plates and the strip member interposed therebetween, the flat faces of the strips are pressed into intimate contact with corresponding marginal portions of juxtaposed plate spaced planar faces and sufficiently such as to exclude atmospheric air presence at contact interfaces therebetween. Atmospheric air pressure acting on plate opposite faces maintains interface contact of the strips with the glass plate faces establishing a leak proof barrier at sides of the cassette preventing any liquid phase of the composition from outflowing through the sides of the cassette during gelling of the composition.

According to feature of the invention, there is further provided a method for assembling a cassette for containing a gel slab used in an electrophoresis separation. Such method comprises providing a pair of flat hard surfaced material plates, said plates having identical rectangular edge envelopes. There is also provided a generally rectangular plate like aligning tool having a flat generally rectangular flat planar upper face, this aligning tool having flanges upstanding from the upper face along each of two adjacent tool side edges, the flanges having inner side faces orthogonal to the tool upper face with said inner side faces intersecting to define a flange inner corner. One of said plates is positioned on the tool upper face with a planar bottom edge of the plate in contact with the inner side face of one of the tool flanges and an adjacent planar side edge of the plate urged into contact the inner side face of the other tool flange so that an exterior corner defined by an intersection of an end of said plate bottom edge with an end of said plate side edge adjacent thereto is in abutment with the flange interior corner. An exterior corner edge of an elongated spacer strip defined by a strip transverse end edge and an adjacent strip longitudinal side edge is positioned in abutment with the flange interior corner so that a planar face of the strip transverse end edge and a planar face of the said strip adjacent longitudinal side edge lie in common planes with the respective plate bottom edge and plate side edge. The spacer strip is of a uniformly thick flexible polymeric material presenting opposite flat faces being of at least coextensive length with said plate side edge. Said one plate is then rotated on the tool to position the plate bottom edge in contact with the inner side face of the said other tool flange and an opposite planar plate side edge in contact with the inner side face of the said one tool flange. An exterior corner edge of a second spacer strip like the first is then positioned in abutment with the flange interior corner so that a planar face of a second strip end edge and a planar face of a second strip longitudinal side edge lie in a common plane respectively with the plate bottom edge and said plate opposite side edge. The other of said plates is then positioned in the tool with a planar side edge thereof abutting the inner side face of the said other tool flange and a said other plate bottom planar edge abutting the inner side face of the said one tool flange thereby to juxtapose the two plates and effect registry of the rectangular envelopes of one with that of the other, the polymeric strip material being a smooth polish finished faced component, the juxtaposed plates defining a cassette space into which a liquid-containing gellable composition can be introduced and allowed to gelate. There is then imposed a pressing force against side edge marginal portions of the juxtaposed plates and the spacer strips therebetween therewith to press the opposite smooth polished finished flat faces of the spacer strips into contact with corresponding marginal portions of plate planar faces and sufficient such as to exclude atmospheric air presence at plate face strip face interfaces whereby atmospheric air pressure acting on remote planar faces of the plates maintains interface contact of the strips with the plate faces establishing a leak proof barrier at sides of the cassette preventing any liquid phase of the composition from outflowing through the sides of the cassette during gelling of the composition.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENTS

The present invention allows for the convenient, quick and certain proper assembly of a cassette for containing a gel slab which is used in an electrophoresis separation. The same is effected with ease of component handling, no misalignment of cassette components, and once used, the cassette is readily disassembled cleaned and its parts made available for reuse. Further no complicated mechanical securement devices need be employed to hold sandwich configuration during gel slab casting and particularly such ones as would pass through the cassette structure itself.

Figure 1:
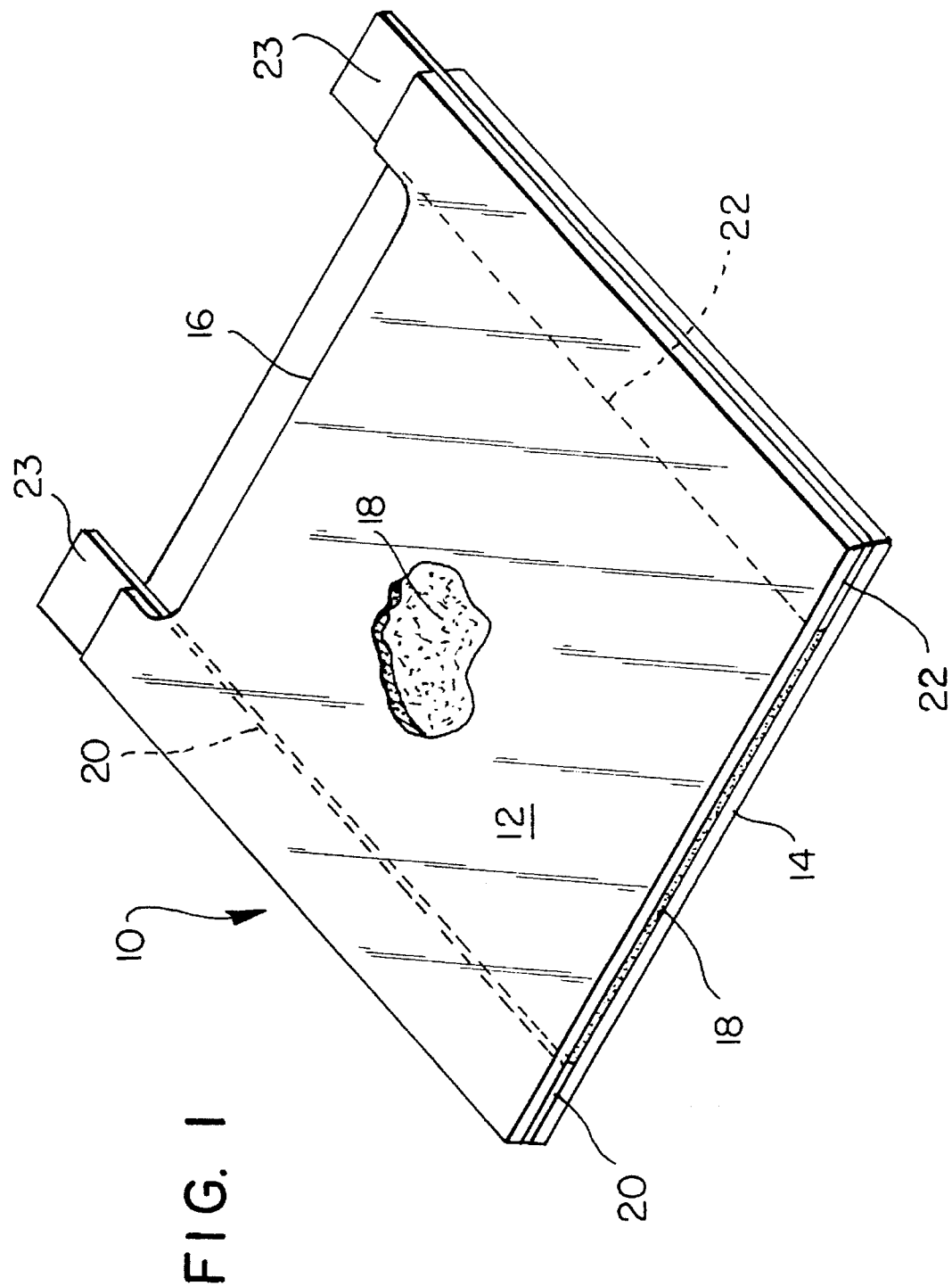
FIG. 1 is a perspective view with a portion broken away of a cassette for containing a gel slab used in an electrophoresis separation and made in accordance with the invention.

Referring to FIG. 1, the cassette 10 comprises two glass plates 12, 14, the plates having a rectangular edge envelope of top and bottom width about 4 inches and opposite side edges of about 3 and ¼ inches.

it will be understood that such envelope dimension is illustrative only and dependent on the dimensions of a particular gel slab size to be used by the molecular biologist. Gel slab, and as presently used in the art, can, e.g., have a width anywhere in a range of 6 cm to 50 cm and a height in a range 7 cm to 65 cm. According to use requirement, slab thickness can vary between about 0.2 mm to about 3.0 mm. Where glass plates are used, same can have a thickness in a range 1.0 mm to 5.0 mm.

One plate 12 of the two and as is common with such cassettes, will have an upper slotted part as at 16 for accessing a gel slab 18 to deliver molecular sample to wells formed in the slab in known manner preliminary to the separation operation.

The plates 12, 14 are juxtaposed with the respective edge envelopes in registry, and the spacing therebetween maintained by spacer strips 20, 22 at least coextensive with side edges of the plate and being relatively thin, widened flat members presenting opposite flat faces which are in contact with marginal edge portions of confronting planar inner side faces of the plates. The strips can but need not extend beyond the top of the cassette as at 23. It will be understood that while glass plates are preferred, hard surface plates of other material also can be used, e.g., plates of acrylic materials.

The side and bottom planar edges of the plates, and a bottom transverse planar edge and a longitudinal outer side edge of the spacer strips all lie in respective common planes, this precision alignment of such edges being an important facet of the invention and significant in establishment and maintenance of fluid proof seal at the sides of the cassette.

Ease of cassette component handling, assembly and preclusion in use of liquid flow outwardly from casting composition through the cassette side is derived from use of spacer strips 20, 22 made from a uniformly thick flexible film of a polymeric material. The strip material further is a double rolled, smooth polish finished pliant faced component. As a result of having such highly polished face and due to the nature of the polymeric material selected, the strip opposite side faces can be intimately interfaced with the planar faces of the plates 12, 14.

This intimate interfacing is produced with pressing force imposed on the sandwiched elements at the side margin portions in way that forces atmospheric air outwardly from the interfacing plate/strip areas and results in a holding together of the sandwiched elements due to atmospheric air pressure acting to press the plate side edge marginal portions against the strip faces. It will be appreciated that the ultra smooth face condition of the spacer strips cooperating with like plate faces is what allows interface intimacy to such degree that air pressure as slight as atmospheric is sufficient to enforce tight contact preventing separation of the strips and glass plates even in face of deliberate digitally applied force trying to cause such a separation. This is an effect akin to that where two clean glass plates are superposed. It is difficult to separate these except by sliding one relative to the other due to hold together force acting on them, this force being much less than present and created with the herein cassette structure.

It is to be understood that no adhesive or any adhesive property of any material is involved is producing the held together assembly of components.

The spacer strip polymeric material preferably is a vinyl and more preferably a polyvinyl chloride. Once such more preferred material is a double rolled polished vinyl film and sheeting product sold by Robeco Chemicals of New York under product designated 40J-0631 which because it is double rolled has a very smooth but pliant face surface, this pliant character contributing to achievement of full face to face conformable contact with the glass plate marginal portion faces. The spacer strips 20, 22 in convenient embodiments can have thicknesses 0.51 mm, 0.76 mm, 1.02 mm, and 1.52 mm all of which sizes are commercially available from Robeco Chemicals.

Once pressed together as noted in the second next above paragraph, the sandwiched elements now constituting a cassette having a space between plates wherein a gel slab can be formed, can be handled by the technician without slippage or risk that in anticipated and necessary following handling, the cassette components could disassemble.

Figure 4:
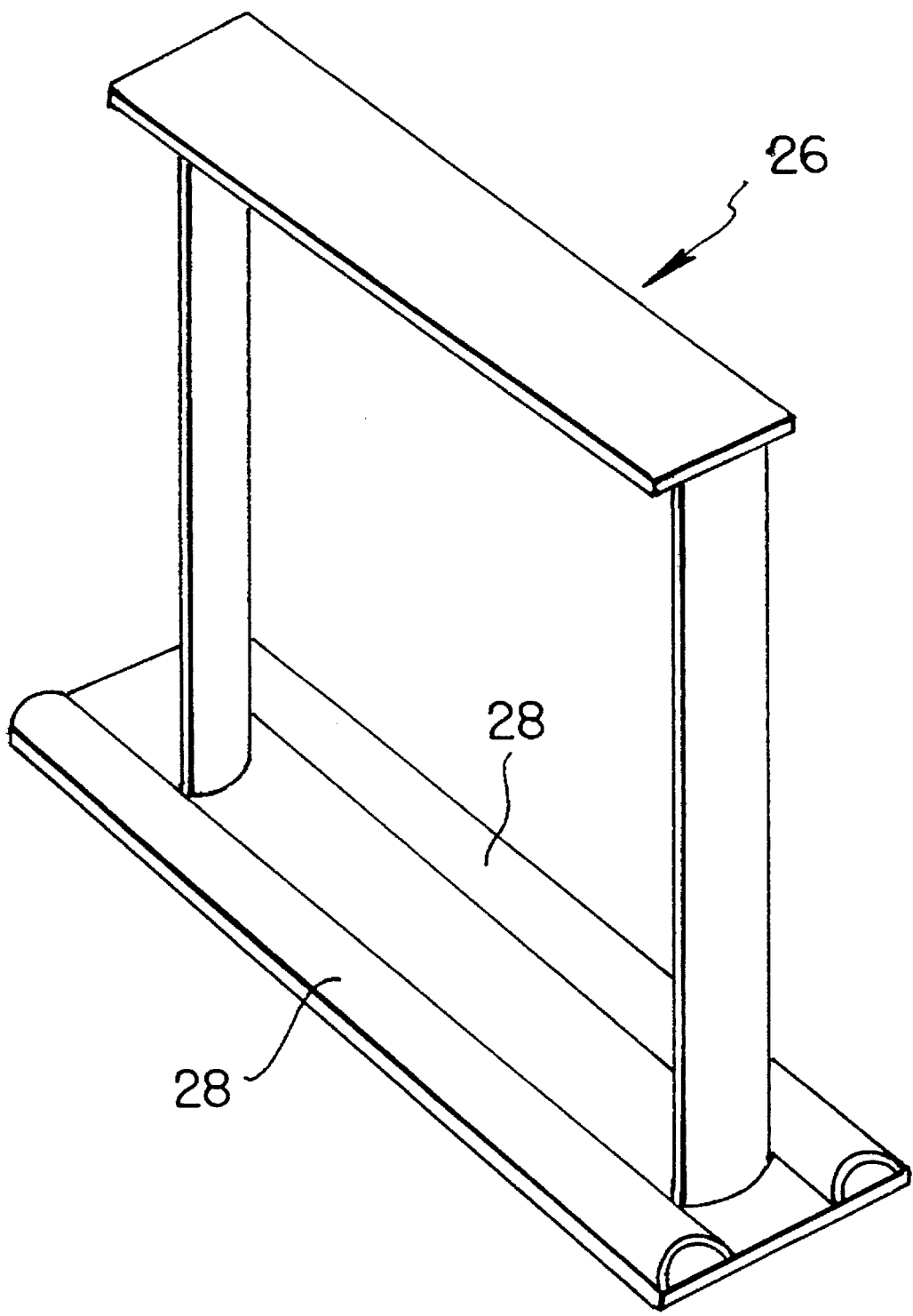
FIG. 4 is a perspective showing of an embodiment of casting stand which can be used when forming a gel slab in a cassette of the invention.

Following cassette assembly, it can be mounted vertically upright in a casting stand 26 as shown in FIG. 4. Casting stands of this type are known and include resilient base seals 28 against which the cassette bottom side is urged during casting to prevent loss of slab casting composition at that location. Further and as commonly practiced, the upper or top edge of plate 14 will be engaged under the top plate of the stand 26 so that plate slotted part 16 is frontally facing to permit pipette introduction of casting composition to the space between the plates.

Figure 2:
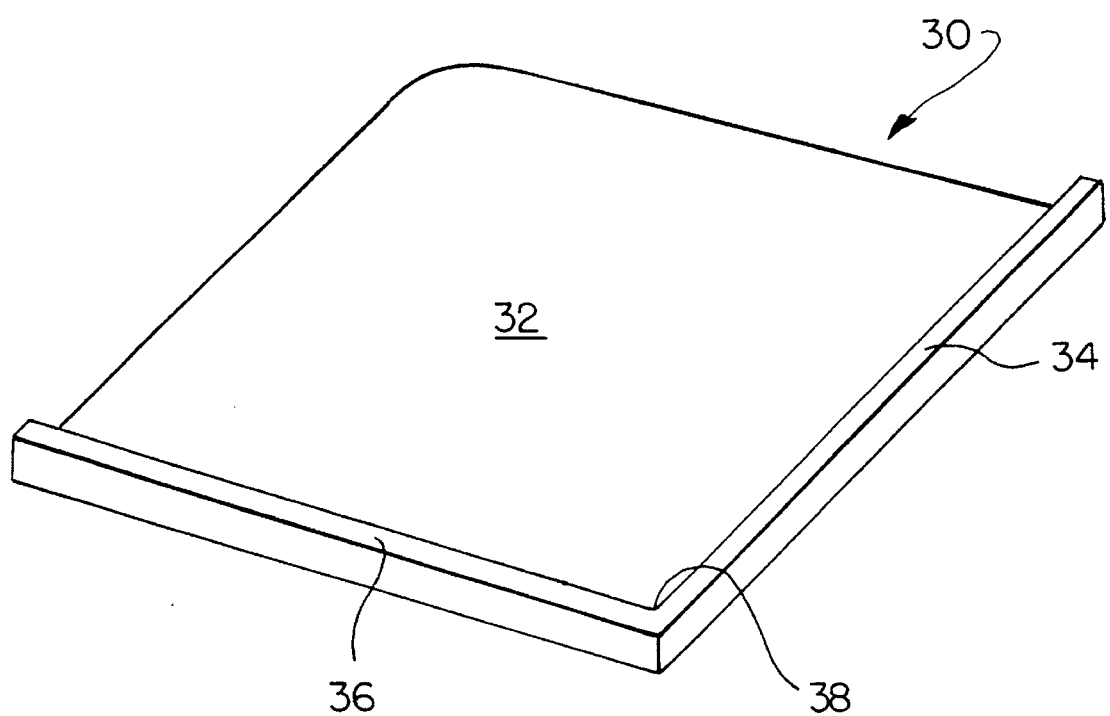
FIG. 2 is a perspective view of an aligning tool provided in accordance with the invention and used in assembling a cassette.

The method of assembling cassette 10 now will be described. Referring to FIG. 2, there is provided an alignment tool 30 which is of flat generally rectangular shape and has a planar upper face 32, and flanges upstanding orthogonally from the face 32 a distance (at least as much and preferably slightly more than a thickness of a cassette to be assembled), the flanges 34, 36 being arranged along two adjacent tool side edges and each flange having an inner planar face, the flanges intersecting at an interior or inner corner as at 38.

Figure 3A:
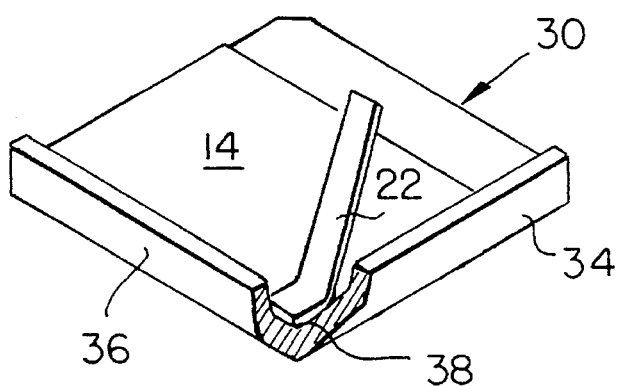
FIGS. 3a–3e are perspective showings of the several steps involved in assembling a cassette.
Figure 3B:
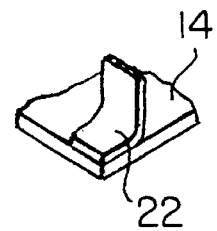

As seen in FIG. 3a, one plate 14 will be positioned in the tool 30, e.g., with the plate bottom edge and a plate right side edge urged into contact with the inner side faces of the flanges 34,36 respectively so the exterior corner formed by these plate edges are in abutment with flange inner corner 38. An exterior corner edge at the bottom of a spacer strip 22 is positioned over the plate with the strip corner edge abutting the tool corner 38. This lines up the strip bottom edge planar with the bottom edge of the plate 14, and a longitudinal edge of the strip with that of the plate right side. This alignment is depicted in FIG. 3b.

Figure 3C:
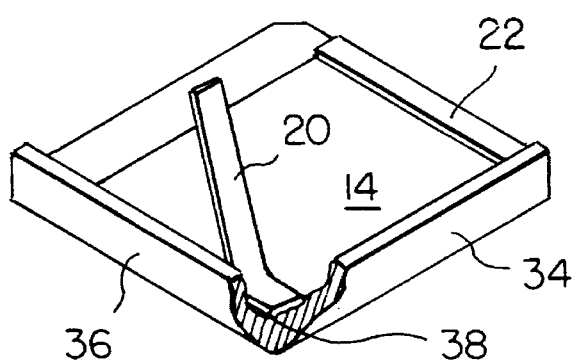
Figure 3D:
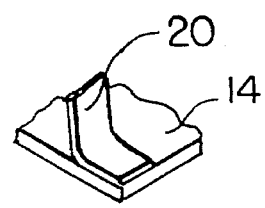

Plate 14 is then rotated on the tool holder to the position shown in FIG. 3c to bring its left side edge in contact with the inner face of flange 34 and its bottom edge in contact with the inner face of flange 36. Spacer strip 20 is then positioned in like manner as with spacer strip 22 so that a bottom edge of strip 20 aligns with the plate bottom edge and a side edge of that strip with the plate left side edge as seen in FIG. 3d.

Figure 3E:
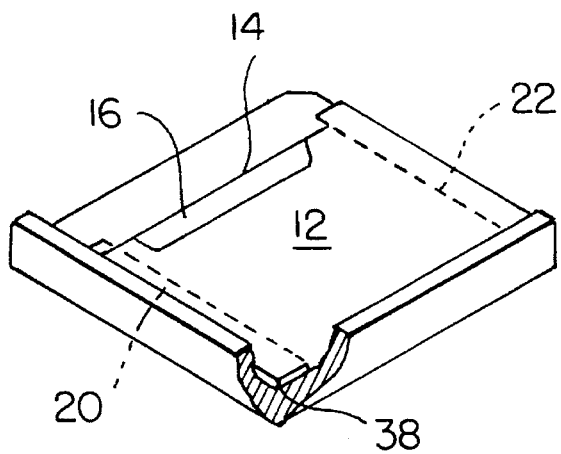

Then and as seen from FIG. 3e, plate 12 is position on the tool over the two strips 20, 22 and with the edge envelope thereof in registry with that of plate 14 such registration being facilitated by urging of the plate against the inner faces of the flanges. The alignment achievements for cassette assembly are made possible with use of the tool and the technician need exercise no special digital skill to do this. The cut out top of the plate 12 as seen in FIG. 3e is oriented at the top of the sandwich. Following mounting of plate 12 pressing of its marginal side edge portions downwardly against the spacers 20, 22 effects the held together condition of the components as described above and with the result that thereafter the technician can remove and handle the cassette with surety and no alteration of the assembled character thereof. Slab casting then can follow.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A cassette for containing a gel slab used in an electrophoresis separation, said cassette comprising:

a pair of hard surfaced plates, the plates each having opposite broad planar faces, a bottom edge and opposite side edges disposed orthogonal to the bottom edge, and spacer means interposed between the plates for holding said plates juxtaposed with a face of one plate spaced from a face of the other plate so as to define a cassette space into which a liquid-containing gellable composition can be introduced and allowed to gelate to form a gel slab, the plates having identical rectangular edge envelopes so that when juxtaposed the bottom and respective side edges of one plate are in alignment with the bottom and respective side edges of the other plate, the spacer means comprising a pair of thin widened strip members of substantially uniformly thick flexible polymeric material presenting opposite flat faces and arranged with one strip member extending at least coextensively with one aligned pair of plate side edges and the other strip member extending at least coextensively with the other aligned pair of plate side edges, each strip member having a longitudinal side edge aligned with corresponding plate side edges, the polymeric strip material being further characterized by being a smooth polish finished pliant faced component so that when a digitally applied squeeze together force is imposed on side edge marginal portions of the juxtaposed plates and the strip members interposed therebetween, the flat faces of the strip members are pressed into intimate contact with corresponding marginal portions of juxtaposed plate spaced planar faces and sufficiently such as to exclude atmospheric air presence at contact interfaces therebetween whereby atmospheric air pressure acting on plate opposite faces maintains said plates and said strip members in held together sandwiched assembly and with interface contact of the strips with the plate faces establishing a leak proof barrier at sides of the cassette preventing any liquid phase of the composition from outflowing through the sides of the cassette during gelling of the composition.

2. A cassette in accordance with claim 1 in which the polymeric strip material is a double rolled polished vinyl film.

3. A cassette in accordance with claim 2 in which the vinyl is a polyvinyl chloride.

4. A cassette in accordance with claim 1 in which the strip members have a thickness in a range of about 0.2 mm to about 3.0 mm.

5. A cassette in accordance with claim 4 in which the plates are of glass.

6. A cassette in accordance with claim 5 in which the glass has a thickness in a range of about 1.0 mm to about 5.0 mm.

7. A cassette in accordance with claim 6 in which a gel slab formed in the cassette has a width in a range of about 6 cm to about 50 cm, and a height in a range of about 7 cm to 65 cm.

* * * * *

UNITED STATES PATENT AND TRADEMARK OFFICE
CERTIFICATE OF CORRECTION

PATENT NO. : 5,525,202

DATED : June 11, 19961995

INVENTOR(S) : Robert EVANS et al.

It is certified that an error appears in the above-identified patent and that said Letters Patent is hereby corrected as shown below:

Cover Page, Item [75], change "Nicolas Neckelmann" to --Skjold Nicolas Neckelmann--.

Signed and Sealed this

Eleventh Day of March, 1997

*Attest:*

BRUCE LEHMAN

*Attesting Officer*  *Commissioner of Patents and Trademarks*